(12) United States Patent
Barri et al.

(10) Patent No.: US 7,476,551 B2
(45) Date of Patent: Jan. 13, 2009

(54) DIAGNOSING ATHEROSCLEROSIS RISK BY MEASURING CARBAMYLATED LOW DENSITY LIPOPROTEIN LEVELS

(75) Inventors: Yousri M. Barri, Plano, TX (US);
Sudhir V. Shah, Little Rock, AR (US);
Alexei G. Basnakian, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 415 days.

(21) Appl. No.: 10/228,493

(22) Filed: Aug. 27, 2002

(65) Prior Publication Data
US 2003/0045004 A1 Mar. 6, 2003

Related U.S. Application Data

(60) Provisional application No. 60/315,101, filed on Aug. 27, 2001.

(51) Int. Cl.
*G01N 33/53* (2006.01)
(52) U.S. Cl. .................. 436/547; 435/7.1; 435/7.92; 435/12; 435/287.2; 435/967; 436/548; 436/15; 436/16; 436/74; 436/177; 436/811
(58) Field of Classification Search ............. 435/7.1, 435/12, 287.2, 967, 7.92; 436/547, 548, 436/506, 15, 16, 74, 177, 811, 174
See application file for complete search history.

(56) References Cited

U.S. PATENT DOCUMENTS 6,309,888 B1 * 10/2001 Holvoet et al. ............... 436/71

OTHER PUBLICATIONS

Roxborough et al., Carbamylation of Proteins and Atherogenesis in Renal Failure, Medical Hypotheses, 45: 125-128 (1995).*

(Continued)

*Primary Examiner*—Gailene R Gabel
(74) *Attorney, Agent, or Firm*—Benjamin Aaron Adler

(57) ABSTRACT

The present invention provides a method of determining whether an individual is at risk for atherosclerosis, comprising the step of: measuring the level of carbamylated LDL in a sample obtained from said individual. Further provided is a method of reducing carbamylation in an individual in need of such reducing, comprising the step of: treating said individual with a monomeric amino acid or another enzymatic or non-enzymatic inhibitor of carbamylation. Also provided is a method of preventing carbamylation in an individual with normal renal function, comprising the step of: treating said individual with a monomeric amino acid. Further provided is a method of treating or preventing atherosclerosis in an individual in need of such reducing, comprising the step of: inhibiting aggregation and/or deposition of carbamylated LDL in said individual.

2 Claims, 11 Drawing Sheets

OTHER PUBLICATIONS

Gonen et al., Abnormal Cell-Interactive Properties of Low-Density Lipoproteins Isolated From Patients with Chronic Renal Failure, Metabolism 34 (1): 10-14 (Jan. 1985).*

Curtiss L. K., Generation of Region-specific Antibodies to Modified Proteins. Journal of Clinical Laboratory Analysis, 1 (3): 266-271 (1987).*

Steinbrecher et al., Immunogenicity of homologous low density lipoprotein after methylation, ethylation, acetylation, or carbamylation: generation of antibodies specific for derivatized lysine, Journal of lipid research, 25 (10): 1109-1116 (Oct. 1984).*

Strongin, Sensitivity, Specificity, and Predictive Value of Diagnostic Tests: Definitions and Clinical Applications, Laboratory Diagnosis of Viral Infections, Lennette, E., ed., Marcel Dekker Inc., New York, pp. 211-219 (1993).*

* cited by examiner nLDL  cLDL  oxLDL  coxLDL 0 min    15 min    30 min    60 min    120 min    240 min Native LDL  Carbamylated LDL Native LDL  Carbamylated LDL

Normal LDL

Carbamylated LDL

DIAGNOSING ATHEROSCLEROSIS RISK BY MEASURING CARBAMYLATED LOW DENSITY LIPOPROTEIN LEVELS

CROSS-REFERENCE TO RELATED APPLICATION

This non-provisional patent application claims benefit of provisional patent application U.S. Ser. No. 60/315,101, filed Aug. 27, 2001.

BACKGROUND OF THE INVENTION

1. Field of the Invention

The present invention relates generally to the field of cardiovascular physiology and atherosclerosis. More specifically, the present invention relates to the prevention and treatment of atherosclerosis using reducing the carbamylation of LDL or the effects of carbamylated LDL.

2. Description of the Related Art

Atherosclerosis is the main cause of many cardiovascular diseases in humans. Atherosclerosis is initiated by injury to cells of the vascular wall. One group of patients that is very susceptible to atherosclerosis is patients with renal insufficiency [1-3]. Patients with end-stage renal disease (ESRD) are at several-fold increased risk of developing cardiovascular pathology because of accelerated atherosclerosis. [1,2]. Even patients with mild renal insufficiency are at 2-3-fold higher risk of cardiovascular disease [3]. The high rate of cardiovascular complications cannot be entirely explained by the known cardiovascular risk factors in these patients.

There is a large body of data which indicates that an atherosclerotic lesion starts when the vascular endothelium is injured. The injured endothelium expresses adhesion molecules for the monocytes to bind to, and the monocytes burrow beneath the endothelial cell layer, ingest modified LDL, and form so-called "foam cells". This process leads to the atherosclerotic plaque, which consists of a mass of lipid-engorged monocytes and macrophages covered by a fibrous cap being pushed out into the vessel lumen by proliferating smooth muscle cells [4-6].

When decrease renal function occurs, the increased amount of urea undergoes spontaneous (chemical, non-enzymatic) transformation to cyanate, which accumulates in patients with chronic renal failure (CRF). Cyanate acts as a potential toxin, inducing a modification of proteins called "carbamylation" [see reviews 7-9].

An example of the carbamylation reaction of free amino groups of protein N-termini is shown in FIG. 1. This reaction is 50 to 100 times faster with α-amino groups of amino acids than with ε-amino groups [7]. Isocyanic acid, the active form of cyanate, reacts irreversibly with nonprotonated groups of amino acids forming α-amino-carbamylation acids from free amino acids. The irreversible carbamylation forming α-amino-carbamyl-lysine occurs in multiple lysine sites within a protein with accumulation over the life span of the protein. When a molecule of cyanate is removed by carbamylation, a new molecule of cyanate is formed because of the equilibrium between urea and cyanate. Reversible carbamylation occurs also at the hydroxyl groups of tyrosine, serine, or threonine, and the sulfhydryl groups of cysteine.

Very few studies have been aimed at the prevention of carbamylation, and all of them have involved lens protein [14, 15]. Incubation of rat lens in cyanate induces an aspirin-preventable increase in phase separation temperature [14]. Similarly, ibuprofen was found to induce a dose-dependent decrease in the binding of cyanate to lens protein [15]. It is possible that ibuprofen competes for cyanate binding sites. Aspirin was more effective when it was pre-incubated with lens protein, suggesting a predominantly covalent interaction. Bendazac also inhibits the carbamylation of lens protein when present with cyanate [16]. Therefore only aspirin, ibuprofen, and bendazac have been evaluated as inhibitors of carbamylation. There are no studies in which any amino acid has been used to prevent carbamylation of proteins or lipids.

The prior art is insufficient for prevention and treatment for cardiovascular pathology caused accelerated atherosclerosis in normal individuals and deficient in the lack of an effective prevention and treatment of individuals with renal disease. The present invention fulfills this long-standing need and desire in the art.

SUMMARY OF THE INVENTION

Patients with certain diseases such as renal disease are at an increased risk of developing cardiovascular events because of accelerated atherosclerosis. The high rate of cardiovascular complications cannot be explained entirely by the known cardiovascular risk factors in these patients. There is a large body of data that indicates that an atherosclerotic lesion starts when endothelium is injured. Blood urea dissociates to form cyanate, which reacts with proteins by a process known as carbamylation. The present invention discloses that carbamylated LDL-cholesterol (cLDL) causes endothelial cell damage, and would thus lead to accelerated atherosclerosis and significant contribution to cardiovascular complications in patients with renal failure. An additional contributory factor is related to carbamylated LDL forming more aggregates than native LDL-cholesterol (nLDL) resulting in its deposition in the arterial wall.

The present invention discloses that lysine, glycine and arginine prevent carbamylation. The present invention further discloses that agents that inhibit or reduce carbamyation or prevent its aggregation or the effects of carbamyation provide new modalities for the treatment of cardiovascular complications in patients with renal disease. Since urea is normally present in the blood of all humans, carbamylated LDL may also play an important role in atherosclerosis in individuals with normal kidney function.

One embodiment of the instant invention discloses a method of determining whether an individual is at risk for atherosclerosis, comprising the step of measuring the level of carbamylated LDL in a sample obtained from said individual.

In another embodiment of the instant invention, a method is provided of assessing the effectiveness of a treatment for an atherosclerosis-related disease in an individual in need of such assessment, comprising the step of monitoring carbamylated LDL and/or antibody to carbamylated LDL in said sample.

Yet another embodiment of the instant invention provides a method of reducing carbamylation in an individual in need of such treatment, comprising the step of treating said individual with enzymatic or non-enzymatic inhibitors of carbamylation.

In yet another embodiment of the instant invention, a method is provided of reducing carbamylation in an individual in need of such treatment, comprising the step of treating said individual with a monomeric amino acid.

In yet another embodiment of the instant invention, a method of treating or preventing atherosclerosis in an individual in need of such inhibition, comprising the step of inhibiting aggregation and/or deposition of carbamylated LDL in said individual, is provided.

Yet another embodiment of the instant invention provides a method of inhibiting atherosclerosis in an individual in need of such inhibition, comprising the step of preventing endothelial cell and/or vascular smooth muscle cell damage caused by carbamylated LDL in said individual.

In still another embodiment of the instant invention, a method of preventing carbamylation in an individual with normal renal function is provided, comprising the step of treating such an individual with a monomeric amino acid.

Moreover, further aspects will be apparent from the following description of the embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIG. 8 shows reactivity of rabbit antisera raised to LDL isoforms.

DETAILED DESCRIPTION OF THE INVENTION

Figure 1:
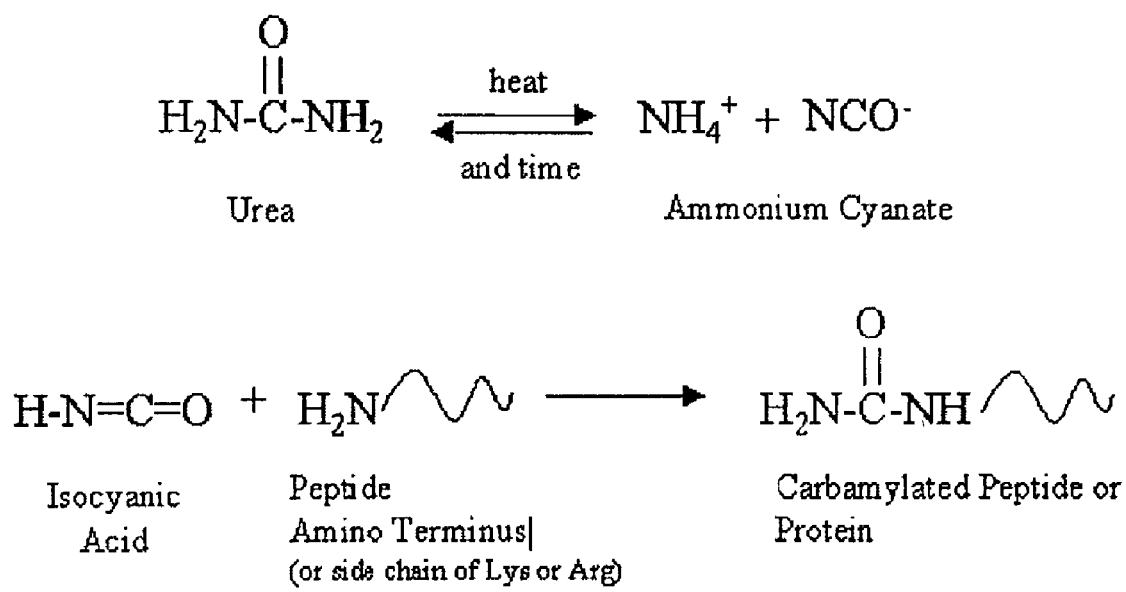
FIG. 1 shows an example of the carbamylation reaction of free amino groups of the N-terminal protein.

Carbamylated low density lipoprotein cholesterol (cLDL), by virtue of its ability to cause endothelial cell damage, leads to accelerated atherosclerosis and contributes significantly to cardiovascular complications in patients with renal failure. An additional contributory factor is related to caramylated LDL-cholesterol forming more aggregates than native LDL-cholesterol (nLDL), resulting in its deposition in the arterial wall. In addition, because urea is normally present in the blood of all humans, crabamylated LDL may also play an important role in atherosclerosis in individuals with normal kidney function.

The instant invention is directed to a method of determining whether an individual is at risk for atherosclerosis, comprising the step of measuring the level of carbamylated LDL in a sample obtained from the individual. Preferably, when the level of carbamylated LDL in the sample is greater than normal as established by standard laboratory methodology in subjects with no known vascular or renal disease, the individual is at risk for atherosclerosis. Generally, the sample is selected from the group consisting of plasma and urine. The level of carbamylated LDL in the sample is determined using an antibody to carbamylated LDL, autoimmune antibody to carbamylated LDL, or any other method known to a person having ordinary skill in this art.

The instant invention is directed to a method of assessing the effectiveness of a prevention and treatment for an atherosclerosis-related disease in an individual in need of such assessment, comprising the step of monitoring carbamylated LDL and/or antibody to carbamylated LDL in the sample.

The present invention describes that cLDL causes endothelial dysfunction and other effects that are linked to atherosclerosis, and therefore, a central premise of the present invention centers on a reduction of cLDL by any means as a beneficial treatment. Accordingly, the present invention is further directed to a method of treating an individual having an undesirably high level of carbamylated LDL by reducing or inhibiting carbamylation in the individual. This method comprises the step of removing carbamylated LDL from the blood or from the individual's body. Thus, it is possible for example to remove cLDL in dialysis patients or other patients by immunophoresis (passing blood plasma through immmunosorbent) or by using a scavenger of carbamylated LDL in vivo.

The instant invention is directed to a method of reducing carbamylation in an individual in need of such reducing treatment, comprising the step of treating the individual with enzymatic or non-enzymatic inhibitors of carbamylation.

The present invention is directed to a method of reducing carbamylation in an individual in need of such reducing treatment, comprising the step of treating the individual with a monomeric amino acid. Representative examples of useful monomeric amino acids include lysine, glycine, and arginine.

Preferably, the amino acid is administered in a dose of from about 5 mg/kg to about 500 mg/kg. In one aspect, this method is useful for treating an individual susceptible to atherosclerosis. In another aspect, this method is useful for treating an individual with renal disease such as an individual with advanced renal failure requiring dialysis and/or transplantation.

The present invention is also directed to a method of treating or preventing atherosclerosis in an individual in need of such inhibition, comprising the step of inhibiting aggregation and/or deposition of carbamylated LDL in the individual. In one aspect, such treatment or prevention of atherosclerosis may comprise preventing cell damage caused by carbamylation of LDL in the the individual, such as endothelial cell and/or vascular smooth muscle cell damage, or the adhesion of monocytes.

The present invention is additionally directed to a method of preventing carbamylation in an individual with normal renal function, comprising the step of treating such an individual with a monomeric amino acid. Representative examples of useful monomeric amino acids include lysine, glycine, and arginine.

The present invention is also directed to an antibody directed against carbamylated LDL. Such an antibody could be either monoclonal or polyclonal. The present invention is also directed to a kit comprising the antibody of the present invention.

The following examples are given for the purpose of illustrating various embodiments of the invention and are not meant to limit the present invention in any fashion.

EXAMPLE 1

Cell culture

Human coronary artery endothelial cells (HCAECs) and vascular smooth muscle cells (VSMCs) were obtained from Clonetics, (Walkersville, Md.). Human coronary artery endothelial cells were maintained in EGM-2-MV medium (Clonetics) and vascular smooth muscle cells were maintained in SmBM medium (Clonetics), both supplemented with 5% fetal bovine serum, growth factors, and antibiotics (gentamycin, amphotericin B). Cells were grown in a humidified incubator (5% $CO_2$, 37° C.), and culture medium was changed every other day. In all experiments, human coronary artery endothelial cells and vascular smooth muscle cells were used at passages between 4 and 7.

EXAMPLE 2

Human native LDL

Human native LDL (nLDL) was purchased from Fluka (Milwaukee, Wis.) and stored at +4° C. in nitrogen atmosphere to prevent oxidation.

EXAMPLE 3

Carbamylated LDL

Carbamylated LDL (cLDL) was produced by chemical modification of nLDL. Native LDL was incubated under sterile conditions with potassium cyanate (Aldrich; Milwaukee, Wis.) (20 mg KOCN/mg nLDL) at 35° C. for 4 hours.

Salt was removed by excessive dialysis against 0.15 M NaCl, 0.01% EDTA, pH 7.0 at 4° C. for 48 hours under sterile conditions. To obtain cLDL carbamylated to different degrees, various incubation periods, from 5 to 300 min, were used.

EXAMPLE 4

Oxidized LDL

Oxidized LDL (oxLDL) was obtained by incubation of nLDL at 1.5 mg/ml concentration with freshly prepared sterile 5 µM $CuSO_4$ for 24 hours at 37° C., after removal of EDTA by dialysis in sterile conditions against phosphate-buffered saline (PBS), pH 7.4 for 24 hours at 4° C. The reaction was stopped by adding 200 µM sterile EDTA.

EXAMPLE 5

Carbamylated-oxidized LDL

Carbamylated-oxidized LDL (coxLDL) was obtained by oxidation of cLDL. All modified LDL forms were kept at 4° C. away from light, and used within 2 weeks after preparation.

EXAMPLE 6

Protein concentration

Protein concentration was measured by the BCA protein assay (Pierce; Rockford, Ill.).

EXAMPLE 7

Electrophoresis of LDL isoforms

Electrophoresis of LDL isoforms was carried out in 0.5% agarose gel in barbital buffer, pH 8.6 for 1 hour (7 µg LDL protein/well, 90 V, 70 mA), and the bands were stained in Sudan Black B.

EXAMPLE 8

Assessment of carbamylation

Assessment of carbamylation was made (a) on the basis of relative electrophoretic mobility in agarose gel, and (b) by the homocitrulline assay as described by Trepanier, et al. .[10]. Briefly, 25 µg of LDL protein in PBS, pH 7.4 (50 µl volume) was incubated with 2 µg proteinase K and 1% SDS (v:v) at 37° C. for 2 hours. Then 250 µl of urea-nitrogen reagent (0.83 M sulfuric acid, 1.13 M orthophosphoric acid, 0.55 mM thiosemicarbazide, 2.6 mM cadmium sulfate), 50 µl 3% diacetyl monoxime in water was added and the mixture was incubated at 97° C. for 30 min. Samples were transferred into a 96-well plate and absorption of chromogen(s) was recorded at 530 nm. Homocitrulline (carbamyl lysine) standard curves (0-30 nmol) were generated using serial dilutions of a stock solution (200 µM) in PBS, pH 7.4. Results are expressed as nmol homocitrulline/mg LDL protein).

EXAMPLE 9

Assessment of oxidation

Assessments of oxidation were made (a) on the basis of relative electrophoretic mobility in agarose gel, and (b) using a thiobarbituric acid reactive substances (TBARS) assay [11]. LDL protein (25 µg in 50 µl PBS) was mixed with 150 µl of freshly prepared 0.67% thiobarbituric acid, 20% trichloroacetic acid and heated at 95° C. for 45 min. Butylated hydroxytoluene (20 μM) and EDTA (100 μM) were added to prevent further oxidation during heating. After cooling the samples to room temperature, 300 μl butanol was added for extraction, and the samples were centrifuged at 4000 rpm for 10 min. The supernatant (200 μL) was transferred into a 96-well plate, and assayed spectrophotometrically at 532 nm in a plate reader. Freshly prepared 1,1,3,3-tetramethoxypropane, which yields malondialdehyde (MDA), was used as a standard. The results are expressed as nmol MDA/mg LDL protein.

EXAMPLE 10

Cell viability

Cell viability was determined by trypan blue exclusion and LDH release as previously described [12]. For the LDH release measurements, the LDH release assay (Promega; Madison, Wis.) was used. Apoptosis was measured using nuclear staining as described and by annexin V/propidium iodide staining. For Annexin V and propidium iodide staining, human coronary artery endothelial cells were cultured ($2 \times 10^5$ cells per well in 6 well plates) in 5% FBS supplemented medium overnight and then treated with LDL. The supernatant and cells obtained with trypsin/EDTA were centrifuged at 1000 rpm for 5 min; cells were combined and washed in PBS, pH 7.4, centrifuged, and resuspended in 200 μl binding buffer. Annexin V (Clontech; Palo Alto, Calif.) (5 μl) and propidium iodide (Clontech) (10 μl) were added and incubated at room temperature in the dark for 15 min. After 300 μl binding buffer was added, FACS analysis was immediately performed using a flow cytometer/cell sorter (Becton Dickinson, Mountain View, Calif.). The percentage of apoptotic cells was calculated by the CELLQUEST software package. Cell viability and proliferation were measured using an MTS assay (CellTiter 96 Aqueous One Solution Cell Proliferation assay kit, Promega Corporation, Madison, Wis.), or a bromodeoxyuridine assay (BrdU cell proliferation assay kit, Oncogene, Cambridge, Mass.). For Western blot analysis, protein samples were resolved by agarose gel electrophoresis as described above. Proteins were electrophoretically transferred to nitrocellulose or to immobilon polyvinylidine difluoride (Millipore, Bedford, Mass.) membranes, and reacted with antibody as described by Towbin [13]. A statistical comparison of the data was carried out using the Student's t-test, and $p < 0.05$ was considered to be significant.

EXAMPLE 11

In vtro carbamylation and oxidation of LDL

Figure 2:
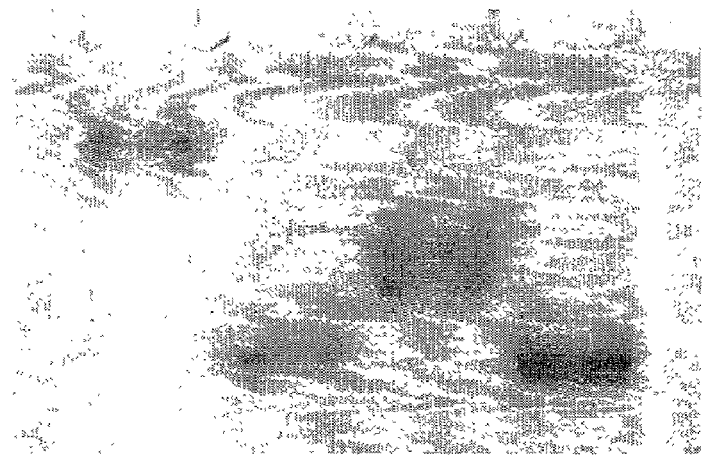
FIG. 2 shows that after human, LDL was carbamylated in vitro in the presence of potassium cyanate (20 mg/mg LDL protein), or oxidized by exposure to 5 µM cupric sulfate, the isoforms have different mobility in agarose gel.

Human LDL was carbamylated in vitro in the presence of potassium cyanate (20 mg/mg LDL protein), or oxidized by exposure to 5 μM cupric sulfate as described above. The isoforms have different mobility in agarose gel (FIG. 2).

EXAMPLE 12

Human LDL-cholesterol can be carbamylated in vitro to different degrees

Figure 3:
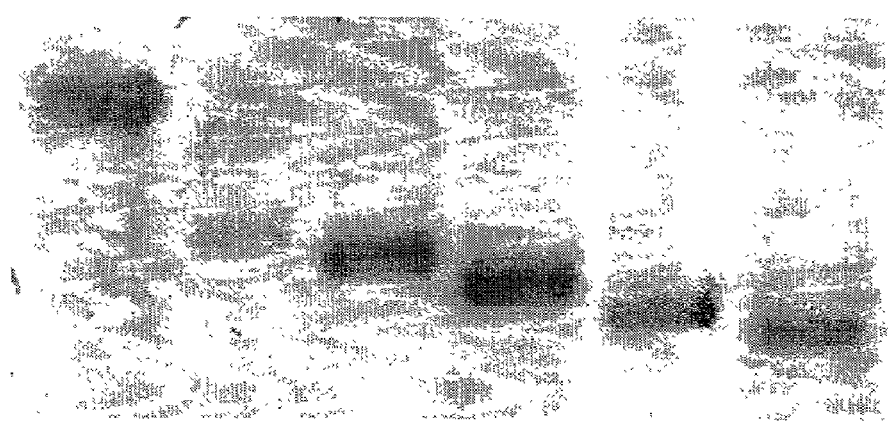
FIG. 3 shows that exposure of human normal LDL to potassium cyanate (20 mg/mg LDL protein) for 15 to 240 minutes led to gradually increased mobility of the carbamylated LDL in agarose gel.

Since the level of LDL carbamylation in humans is not known, it is necessary to have methods to study LDL carbamylated to different degrees. Exposure of human normal LDL to potassium cyanate (20 mg/mg LDL protein) for 15 to 240 min led to gradually increased mobility of the carbamylated LDL in agarose gel (FIG. 3). The degree of carbamylation measured using a homocitrilllune assay was gradually increased from 94±14 nmol homocitrulline/mg LDL protein after 15 min to 221±32 nmol homocitrulline/mg LDL protein after 240 min of carbamylation.

EXAMPLE 13

Carbamylated LDL induces injury to endothelial cells in vitro

Figure 4:
FIG. 4 shows that endothelial cell morphology is changed after treatment with carbamylated LDL. Cells treated with 200 µg/ml carbamylated LDL showed morphological signs of deterioration as compared to cells treated with the same amount of native LDL. The cells look damaged, they are smaller than normal and shrunken, and some of them are detached from the plastic surface. The monolayer is disrupted. Spaces between cells are filled with cellular debris.
Figure 4:
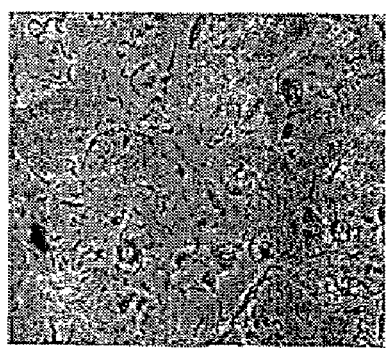
Figure 4:
Figure 4:
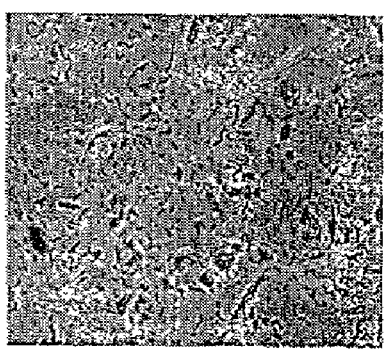

Cultured human coronary artery endothelial cells treated with 50-400 μg/ml cLDL for 24 hours showed, under light microscopy, signs of morphological alterations, detachment and presence of cellular debris (FIG. 4). The cells look smaller (shrunken), which is indicative of apoptosis.

EXAMPLE 14

Carbamylated LDL induces irreversible cell injury

Figure 5:
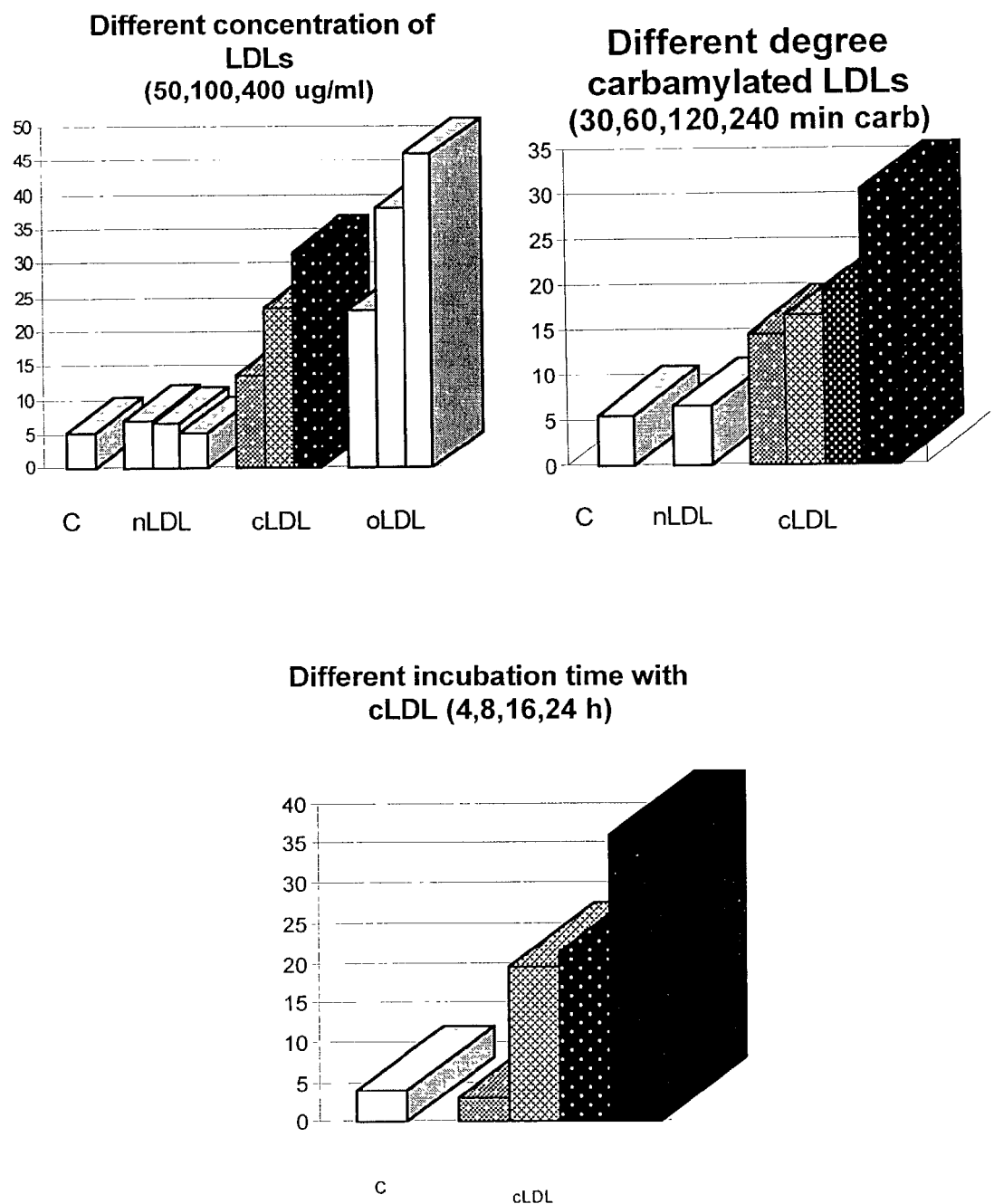
FIG. 5 shows LDH release by cultured human endothelial cells treated with native (nLDL), carbamylated (cLDL), or oxidized LDL (oLDL).

Carbamylated LDL induces irreversible cell injury as measured by LDH release (FIG. 5). This injury was dose- and time-dependent, and correlated with the degree of LDL carbamylation (between 90 and 220 nmol homocitrulline/mg protein). At 200 μg/ml carbamylated LDL, the LDH release was 21.3±4.6% compared to 6.6±3.2% (n=5) induced by native LDL.

EXAMPLE 15

At least part of the cellular population dies by apoptosis

Figure 6:
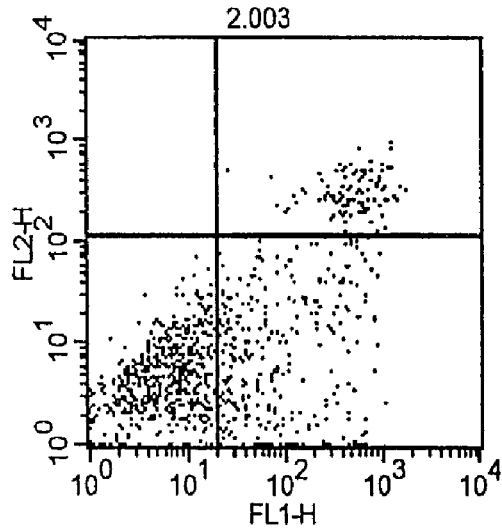
FIG. 6 shows that carbamylated LDL induces apoptosis of human coronary endothelial cells. FACS analysis of endothelial cells stained with propidium iodide/Annexin V after being treated with 200 µg/ml nLDL or 200 µg/ml cLDL for 24 hours. More cells are visible in the lower right quadrant of the plot (annexin V staining).
Figure 6:
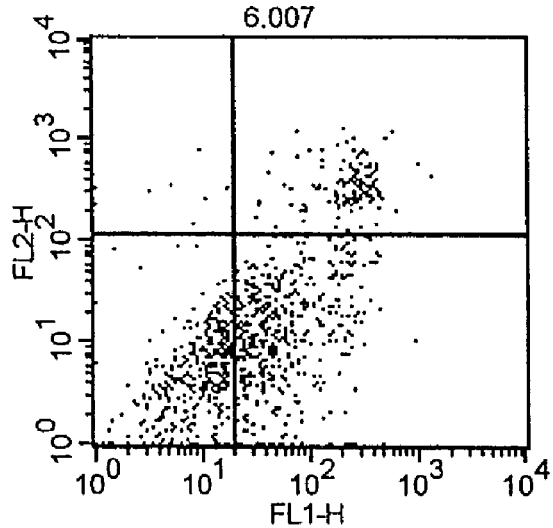

Flow cytometry using Annexin V staining also demonstrated the presence of apoptotic cell death (FIG. 6). The portion of Annexin V-positive cells was 11±2% in non-treated cells, 14±3% in nLDL treated, and 24±4% in cLDL treated cells (200 μg/ml LDL for all isoforms). The cytotoxicity of cLDL was less than that induced by oxLDL in parallel experiments (data not shown).

EXAMPLE 16

In vitro carbamylation of LDL can be inhibited with monomeric amino acids

Figure 7:
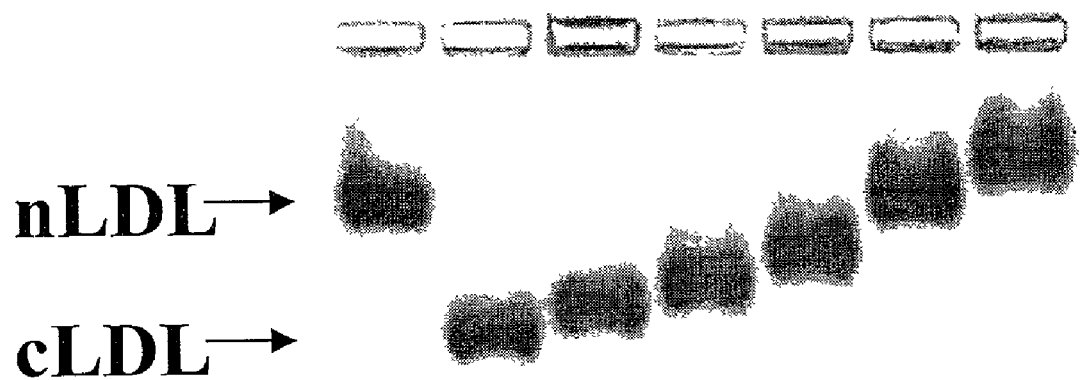
FIG. 7 shows in vitro inhibition of LDL carbamylation with L-lysine.

Monomeric amino acids (L-lysine, L-arginine, L-glycine) can inhibit carbamylation of LDL in vitro when applied in molar ratios of 1:1 to 16:1 (L-lysine:KOCN) (FIG. 7).

EXAMPLE 17

Carbamylation has little or no effect on oxidation of LDL in vitro, and vice versa Gradually carbamylated LDL (90 to 220 nmol homocitrulline/mg protein) was oxidized in vitro and the level of oxidation examined using a thiobarbituric acid reactive substances (TBARS) assay. These results showed that susceptibility of LDL to oxidation was in the range of 60-70 nmol malonaldehyde/mg protein, which was not increased after carbamylation. Instead, some competitive inhibition (up to 20%) between carbamylation and oxidation of lysine residues was observed. Another experiment, in which the LDL was gradually oxidized in vitro and tested for carbamylation, demonstrated no effect of oxidation on carbamylation of the same substrate (data not shown).

EXAMPLE 18

As opposed to native LDL, cLDL is more likely to form aggregates and precipitate from solutions The aggregation in LDL isoforms' solutions was measured using ultrafiltration through 0.22 μm filter or ultracentrifugation at 14,000 g for 10 min. The results presented in Table 1 show that cLDL's ability to form aggregates is higher than that of nLDL. Aggregation of cLDL may contribute to atherosclerotic plaque formation.

TABLE 1

Aggregation of LDL isoforms in solution (% lost during centrifugation or ultrafiltration)

| LDL isoform | Centrifugation | Filtration |
|---|---|---|
| nLDL | 10 | 38 |
| cLDL | 26 | 62 |

EXAMPLE 19

Antibody to carbamylated LDL

Figure 8A:
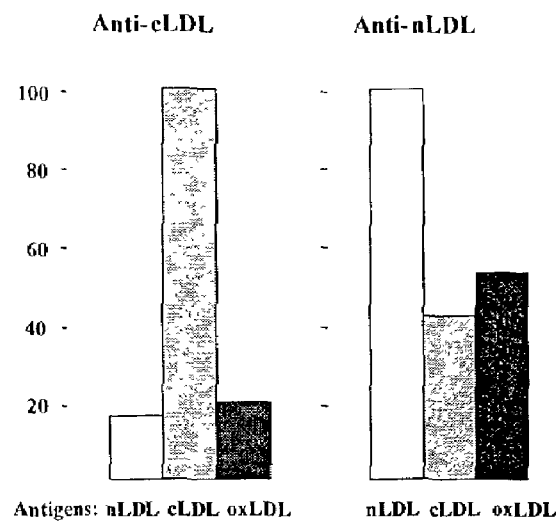
FIG. 8A shows cross-reactivity of cLDL antisera with nLDL and oxLDL and cross-reactivity of nLDL antisera with cLDL and oxLDL.
Figure 8B:
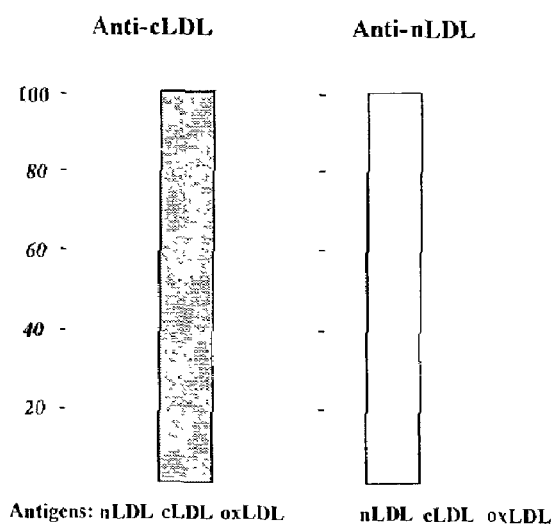
FIG. 8B shows that cLDL and nLDL antibodies can be purified using affinity chromatography so as to lose all of its cross-reactivity.
Figure 9:
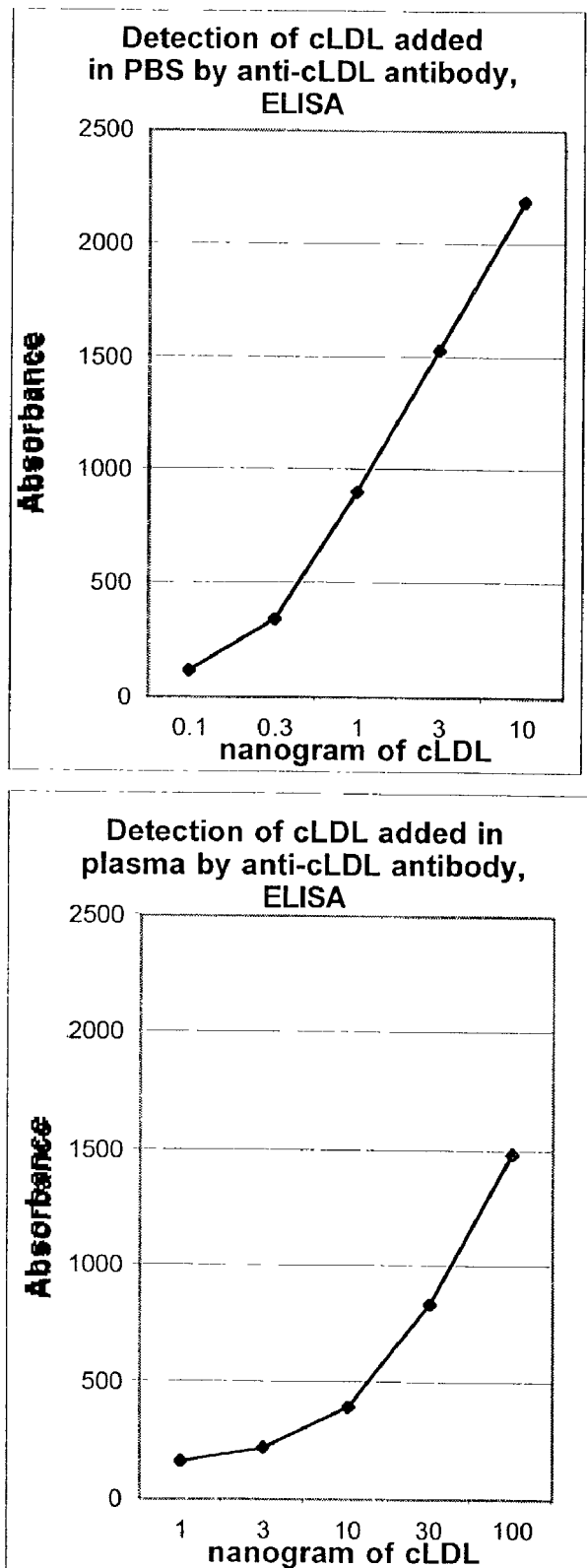
FIG. 9 shows identification of carbamylated LDL in patients with end stage renal disease using Western blotting of human plasma proteins with anti-carbamylated LDL. Patients (P1, P2) but not donors (D1, D2) have a second band (shown by arrow) which reacts with anti-carbamylated LDL and have the mobility of carbamylated LDL in agarose gel.

Antibody to carbamylated LDL is not commercially available. In vitro modified cLDL and oxLDL, as well as nLDL, were used for raising polyclonal antibody in rabbits. Although the obtained antisera analyzed by quantitative Western blotting have some cross-reactivity, both anti-cLDL and anti-nLDL were more specific to their direct antigens (FIG. 8). These antibodies can be purified using affinity (immunosorption) chromatography so as to lose most or all of the cross-reactivity. The antibodies were sensitive enough to detect as little as 30 pg of LDL protein in plasma using an ELISA assay (FIG. 9). Antisera to oxLDL did not have any specificity (data not shown) and was excluded from the studies. If necessary, commercial monoclonal antibody to human oxLDL (Research Diagnostics, Flanders, N.J.) may be used.

EXAMPLE 20

Protein carbamylation is increased in patients with end-stage kidney disease (ESRD)

Although the presence of carbamylated proteins has been reported in patients with renal failure, the presence of cLDL in plasma has not been previously examined. In order to produce a tool for studying cLDL, cLDL was prepared and polyclonal antibodies to cLDL and nLDL was raised in rabbits as described above.

Figure 10:
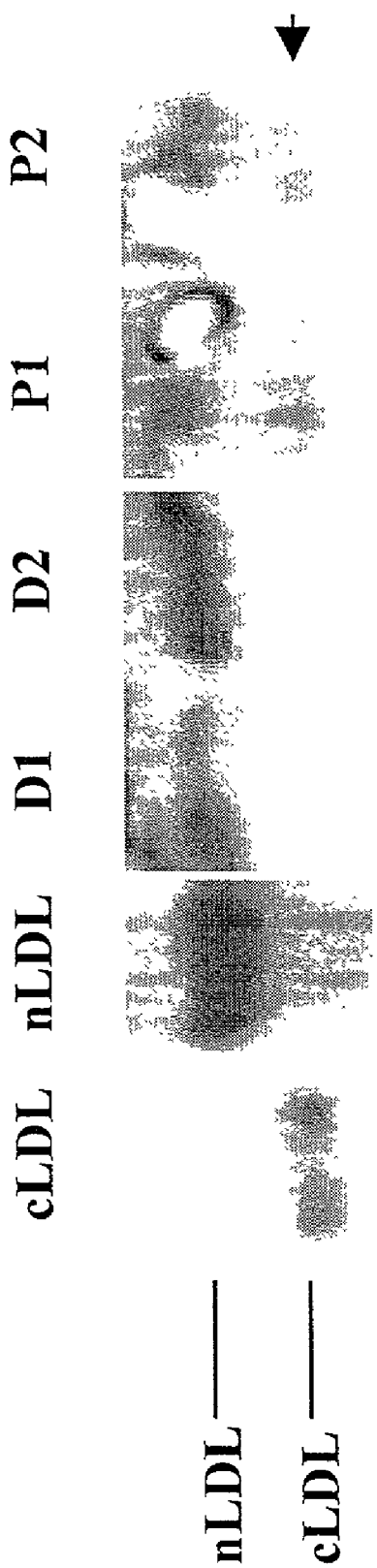
FIG. 10 shows the identification of cLDL in patients with end stage renal disease using Western blotting of human plasma proteins with anti-cLDL. Patients (P1, P2) but not donors (D1, D2) have a second band (shown by arrow) which reacts with anti-cLDL and has the mobility of cLDL in agarose gel.
Figure 11:
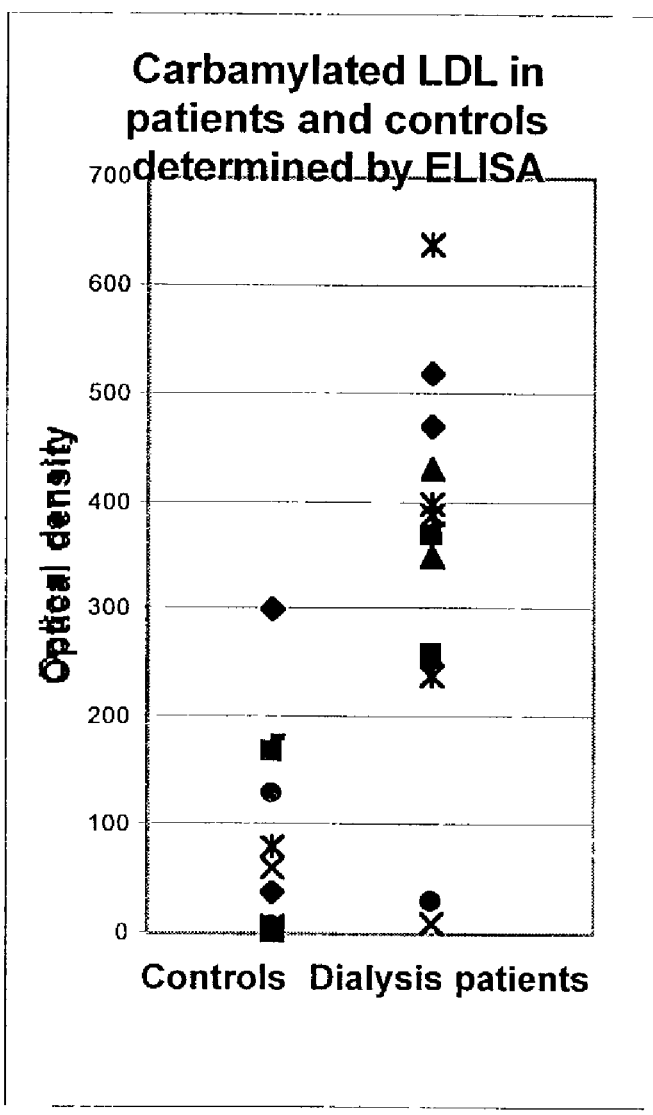
FIG. 11 shows carbamylated LDL in end stage renal disease patients and controls determined by using specific anti-cLDL antibodies. Results are presented as absorbance at 450 nm.

In pilot experiments, plasma from patients with end-stage kidney disease was subjected to electrophoresis in agarose and subsequent immunoblotting with anti-cLDL antibody to detect the presence of modified LDL. The high mobility in agarose (due to increased charge of the molecule as compared to nLDL) corresponding to cLDL, as well as interaction with anti-cLDL antibody, indicates that the modified LDL is cLDL (FIGS. 9, 10). The plasma from the same patients demonstrated increased total levels of carbamylation of lysine residues in proteins (43±6 versus 14±3 nmol homocitrulline/mg protein in donors). The ELISA assay showed a significant increase of cLDL in dialysis patients (absorption: 0.340±0.045, n=15) versus healthy individuals (0.104±0.032, n=9, p<0.01) (FIG. 11). This increase correlated with the elevation of the total carbamylation of proteins in plasma (43±6 vs. 14±3 nmol homocitrulline/mg protein in healthy subjects). A more quantitative assay to measure an antigen, competitive ELISA, also showed that cLDL content in patients is increased (0.350±0.030, n=15, vs. 0.270±0.020, n=15, in healthy individuals, p<0.03).

EXAMPLE 21

Elevation of Autoantibody to carbamylated LDL in dialysis patients

Figure 12:
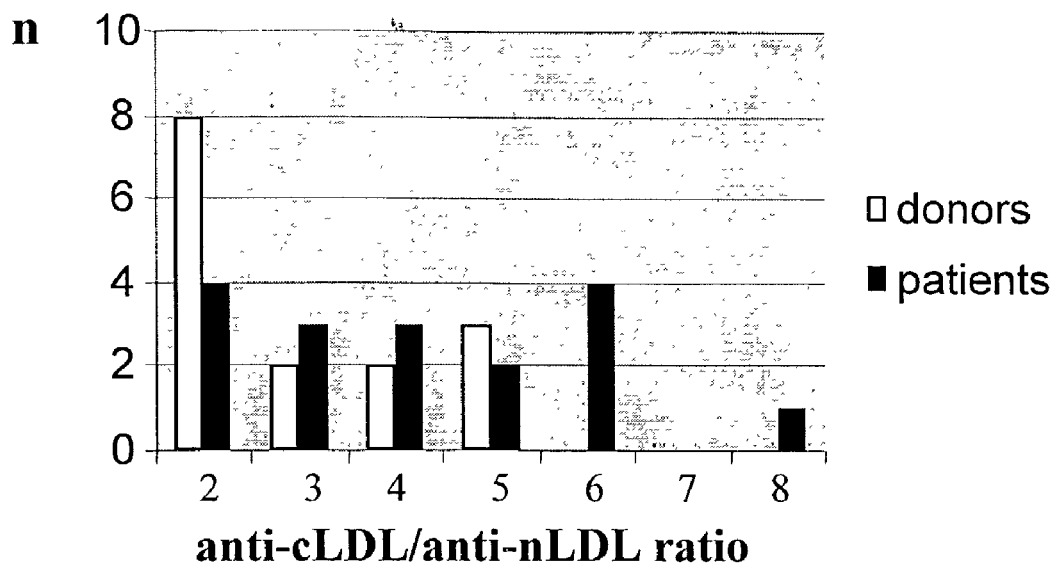
FIG. 12 shows increased anti-cLDL autoantibody (anti-cLDL/anti-nLDL ratio) in end stage renal disease patients.

Carbamylated LDL is highly immunogenic when used as an antigen in rabbits. Both hemodialysis patients and healthy individuals have autoantibodies to cLDL. Increased anti-cLDL antibody was detected (anti-cLDL/anti-nLDL ratio) in patients with chronic renal failure (FIG. 12). Also, in these patients autoantibody to cLDL are mainly against moderately carbamylated LDL, rather than mildly or heavily carbamylated LDLs. Taken together, these data suggest that both elevated cLDL and autoantibody to cLDL are potential pathogenic factors in the development of atherosclerosis in renal patients.

EXAMPLE 22

In addition to cell death, carbamylated LDL induces proliferation of endothelial cells The results of the MTS assay showed significant decreases in the numbers of cells treated with oxLDL and coxLDL, especially at high concentrations (at 200 μg/mL concentration, viability was 12±2% and 4±2%, respectively) (Table 2). On the other hand, the decrease was not seen in the number of cells treated with cLDL despite the presence of high LDH release assay results and assessment of cell injury/death under light microscopy (viability 118% for both nLDL and cLDL).

The results of the bromodeoxyuridine (BrdU) cell proliferation assay showed that cLDL causes a striking proliferation in human coronary artery endothelial cells (at 200 μg/mL, 298% with cLDL, vs. 92% with nLDL). The proliferative effect gradually increased with concentration of cLDL: percentage increases of 121, 209, 298, and 316% were seen with cLDL concentrations of 50, 100, 200, and 400 μg/ml, respectively. While oxLDL did not have a significant proliferative effect at similar concentrations, coxLDL showed a 227% proliferation increase compared to controls, besides a toxic effect similar to or greater than that of oxLDL (Table 3).

TABLE 2

The viability of cells treated with modified LDLs determined by MTS assay.

| | MTS assay Viability (%) | | | |
|---|---|---|---|---|
| | 50 μg/mL | 100 μg/mL | 200 μg/mL | 400 μg/mL |
| Control | 97 ± 2 | | | |
| NLDL | 110 ± 9 | 118 ± 7 | 118 ± 8 | 136 ± 12 |
| CLDL | 102 ± 6 | 115 ± 6 | 118 ± 7 | 143 ± 14 |
| OxLDL | 72 ± 9 | 25 ± 9 | 12 ± 2 | 1.3 ± 0.4 |
| CoxLDL | 71 ± 9 | 21 ± 11 | 4 ± 2 | 0.7 ± 0.5 |

TABLE 3

The proliferation rate of cells treated with modified LDLs

| | BrdU cell proliferation assay Proliferation (%) | | | |
|---|---|---|---|---|
| | 25 μg/mL | 50 μg/mL | 100 μg/mL | 200 μg/mL |
| Control | 75 | | | |
| NLDL | 95 | 97 | 91 | 96 |
| CLDL | 112 | 121 | 209 | 298 |
| OxLDL | 107 | 107 | 106 | 165 |
| CoxLDL | 65 | 107 | 135 | 227 |

EXAMPLE 23

Carbamylated LDL induces both DNA repair and DNA synthesis in endothelial cells.

Flow cytometry of LDL-treated cells double-labeled with BrdU and 7-AAD (marker of total DNA) was performed to detect whether BrdU incorporation is linked to DNA synthesis or DNA repair, and whether mitosis is suppressed, and thus accumulation of polyploid cells is associated with the increase of BrdU incorporation. The data indicated that nLDL induces mainly DNA repair synthesis leading to increased BrdU incorporation in G0/G1 phase without any significant change in cell cycle. In contrast cLDL induces both DNA repair and DNA synthesis (17.0±1.1% vs. 8.3±0.7% and 7.2±1.4% cells in S-phase in nLDL-treated and non-treated cells, respectively). No accumulation of polyploid cells after cLDL or nLDL treatment was observed. Potassium cyanate did not induce proliferation or DNA synthesis in HCAECs. In conclusion, cLDL produces a profound dysfunction of cultured endothelial cells, which in addition to cell death includes DNA damage and the induction of proliferation.

EXAMPLE 24

Carbamylated LDL induces proliferation of vascular smooth muscle cells (VSMCs).

Figure 13:
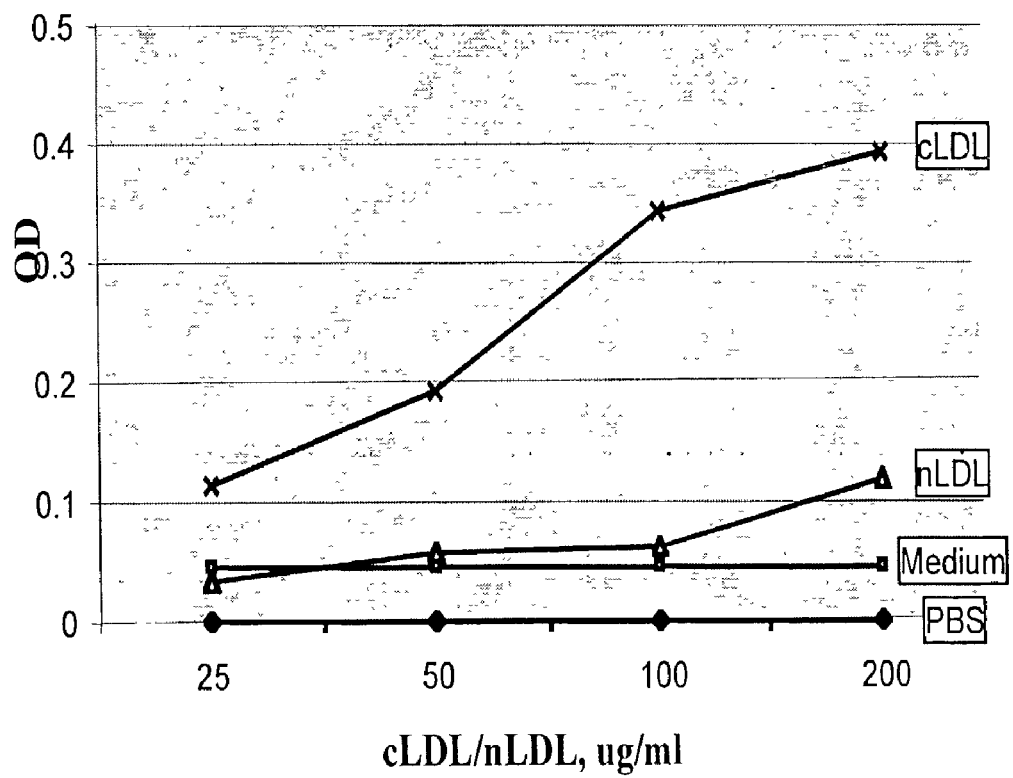
FIG. 13 shows the proliferation of vascular smooth muscle cells in the presence of LDL isoform as measured by a BrdU assay.

Proliferation of vascular smooth muscle cells is a crucial element of the atherosclerotic plaque growth, and thus is very important in the mechanism of atherosclerosis. Carbamylated LDL induces a significant proliferation of vascular smooth muscle cells in vitro in a dose-dependent manner (FIG. 13).

The following references were cited herein.
1. Reikes S T: Trends in end-stage renal disease. Epidemiology, morbidity, and mortality. *Postgrad Med* 108(1): 124-6, 129-31, 135-136, 2000
2. Venkatesan J, Henrich W L: Anemia, hypertension, and myocardial dysfunction in end-stage renal disease. *Semin Nephrol* 17(4):257-269, 1997
3. Culleton B F, Larson M G, Wilson P W F, Evans J C, Parfrey P S, Levy D: Cardiovascular disease and mortality in a community-based cohort with mild renal insufficiency. Kidney Int. 56, 2214-2219, 1999
4. Galle et al.,: Lp(a) and LDL induce apoptosis in human endothelial cells and in rabbit aorta: role of oxidative stress. *Kidney Int* 55(4):1450-61, 1999
5. Mallat Z, Tedgui A: Apoptosis in the vasculature: mechanisms and functional importance. *Br J Pharmacol* 130(5):947-62, 2000
6. Dart A M, Chin-Dusting J P: Lipids and the endothelium. *Cardiovasc Res* 43(2):308-22, 1999
7. Kraus L M, Kraus A P Jr: Carbamoylation of amino acids and proteins in uremia. *Kidney Int* 59 Suppl 78:S102-7, 2001
8. Steinbrecher et al., Immunogenicity of homologous low density lipoprotein after methylation, ethylation, acetylation, or carbamylation: generation of antibodies specific for derivatized lysine. *J Lipid Res* 25(10):1109-16, 1984
9. Weisgraber K H, Innerarity T L, Mahley R W: Role of lysine residues of plasma lipoproteins in high affinity binding to cell surface receptors on human fibroblasts. *J Biol Chem* 253(24):9053-62, 1978
10. Trepanier D J, Thiebert R J, Draisey T F, Caines P S. Carbamylation of erythrocyte membrane proteins: an in vitro and an in vivo study. Clin Chem 29(4): 347-355, 1996
11. Yang et al., Inhibitory effect of Chinese green tea on endothelial cell-induced LDL oxidation. Atherosclerosis 2000; 148: 67-73
12. Ueda N, Walker P D, Hsu S-M, Shah S V: Activation of a 15-kDa endonuclease in hypoxia/reoxygenation injury without morphologic features of apoptosis. Proc Natl Acad Sci USA 92:7202-7206, 1995
13. Towbin H, Staehelin T, Gordon J: Electrophoretic transfer of proteins from polyacrylamide gels to nitrocellulose sheets: Procedure and some applications. Proc Natl Acad Sci 76:4350-4354, 1979.
14. Compton M, Rixon K C, Harding J J. Aspirin prevents carbamylation of lens proteins and prevents cyanate-induced phase separation opacities in vitro: a possible mechanism by which aspirin could prevent cataract. Exp Eye Res 40: 297-311, 1985.
15. Roberts K A, Harding J J. Ibuprofen, a putative anti-cataract drug, protects the len against cyanate and galactose. Exp Eye Res 50: 157-164, 1990.
16. Lewis B S, Rixon K, Harding J J. Bendazac prevents. cyanate binding to soluble lens proteins and cyanate induced phase separation opacities in vitro. A possible mechanism by which bendazac could delay cataract. Exp Eye Res 43: 973-9, 1986.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are. presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of determining whether an individual is at risk for atherosclerosis, comprising:
measuring levels of carbamylated low density lipoprotein cholesterol (cLDL) in a blood plasma sample obtained from said individual and in a blood plasma sample(s) obtained from a healthy individual(s);

comparing the level of cLDL in the blood plasma sample from said individual with the level(s) of cLDL in the blood plasma sample(s) from said healthy individual(s); and determining an increase in the level of cLDL in the blood plasma sample from said individual over the level(s) of cLDL established as normal in the blood plasma sample(s) from healthy individuals, thereby indicating that said individual is at risk for atherosclerosis.

2. The method of claim 1, wherein the level of cLDL in said blood plasma sample is determined using an antibody to cLDL.

* * * * *